(12) United States Patent
Church

(10) Patent No.: US 6,660,901 B2
(45) Date of Patent: *Dec. 9, 2003

(54) CHARCOAL SKIN PATCH

(76) Inventor: Glenda Church, 520 N. Ocean Blvd., #2, Pompano Beach, FL (US) 33062

( * ) Notice: Subject to any disclaimer, the term of this patent is extended or adjusted under 35 U.S.C. 154(b) by 0 days.

This patent is subject to a terminal disclaimer.

(21) Appl. No.: 10/082,937

(22) Filed: Feb. 27, 2002

(65) Prior Publication Data

US 2002/0128579 A1 Sep. 12, 2002

Related U.S. Application Data

(63) Continuation-in-part of application No. 09/405,909, filed on Sep. 24, 1999, now Pat. No. 6,353,145.

(51) Int. Cl.$^7$ .............................................. A61F 13/00
(52) U.S. Cl. .............................. 602/48; 602/41; 602/54; 424/447; 424/448
(58) Field of Search ............ 602/41–59; 424/443–449; 604/304–308

(56) References Cited

U.S. PATENT DOCUMENTS

| | | | | | |
|---|---|---|---|---|---|
| 4,307,717 | A | * | 12/1981 | Hymes et al. ................. | 602/48 |
| 4,715,857 | A | * | 12/1987 | Juhasz et al. ................ | 604/359 |
| 4,756,314 | A | * | 7/1988 | Eckenhoff et al. .......... | 424/443 |
| 5,407,442 | A | * | 4/1995 | Karapasha ................... | 604/359 |
| 6,353,145 | B1 | * | 3/2002 | Church ......................... | 602/48 |

* cited by examiner

*Primary Examiner*—Kim M. Lewis
(74) *Attorney, Agent, or Firm*—Robert M. Downey, P.A.

(57) ABSTRACT

A patch for topical application to the skin includes a charcoal based composition applied to an impervious backing sheet. In a preferred embodiment, the charcoal composition is provided in the form of a slice or layer of generally uniform thickness and includes activated charcoal combined with a host material.

7 Claims, 3 Drawing Sheets

CHARCOAL SKIN PATCH

This application is a continuation-in-part application of patent application Ser. No. 09/405,909 filed on Sep. 24, 1999, now U.S. Pat No. 6,353,145.

BACKGROUND OF THE INVENTION

1. Field of the Invention

The present invention relates to the use of charcoal in human and animal pathology and, more particularly, to a topically applied skin patch containing activated charcoal for adsorbing toxins, bacteria, fungus, carcinogens, and other pathogens in the treatment of bites, stings, injuries, disease and other disorders.

2. Discussion of the Related Art

Charcoal is a black or dark colored porous form of carbon derived from vegetable or animal substances. Charcoal, either wood preserved by charring (i.e. carbo vegetabilis) or organic materials or bones prepared through distillation (i.e. carbo animalis), has many known beneficial properties, such as the ability to adsorb toxic or noxious gasses, disease, germs, fluid toxic wastes and heavy metals. Charcoal is known to be an effective adsorbent of toxins in the body, and is thus capable of cleansing and healing the body. The present invention uses wood base charcoal (i.e. carbo vegetabilis) which contains about 90% carbon. Sources of wood base charcoal include, but are not limited to, willow, eucalyptus, pine, oak and maple.

Activated charcoal is produced by a controlled burning or charring of the starting material, such as wood or bone, and contact with an oxidizing gas, pressurized steam, or a strong acid. Certain electrostatic properties develop in activated charcoal during production which favor the binding of many poisons. The resultant charcoal particles have thousands of crevices, pits, grooves, and holes, which, when opened out, create an enlarged specific surface area that provides an enhanced adsorbtive capacity. In fact, one cubic centimeter of activated charcoal will have a surface area of up to 1,000 square meters.

As described e.g. in a book by A. Thrash, M. D. and C. Thrash, M. D., *Charcoal*, Family Health Publications, LLC, 1988, charcoal compresses containing, in addition to charcoal, corn starch or flax seed have been known for application to body surfaces on a fabric pad, such as for the treatment or palliation of animal stings and bites. Hops or smartweed is known to be added to the charcoal material of such compresses, with fresh or dried leaves added to the charcoal material. These compresses can be applied hot, or a heating pad can be applied over them.

In the related art, U.S. Pat. No. 322,664 discloses a method of producing carbonized vegetable matter, referred to as carbon wool, for an antiseptic dressing. U.S. Pat. No. 2,690,415 relates to an odor adsorbent bandage or dressing for covering odoriferous wounds, corpses and other noxious bodies. The bandage has an adhesive coated web, such as gauze and an odor absorbent material, such as activated carbon.

Objects and Advantages of the Invention

It is a primary object of the present invention to provide a safe and inexpensive product for topical application to the skin in order to adsorb toxins.

It is a further object of the present invention to provide a safe and inexpensive skin patch containing activated charcoal for adsorbing toxins, bacteria, fungus, carcinogens, and other pathogens.

It is still a further object of the present invention to provide a safe and inexpensive skin patch containing activated charcoal which adsorbs toxins, bacteria, fungus, carcinogens and other harmful pathogens in the treatment of bites, stings, injuries, disease and other disorders.

It is yet a further object of the present invention to provide a safe and inexpensive charcoal skin patch which is adapted to remove poison and inflammation of the skin tissue caused from poison plants, insects, and reptiles, such as poison ivy, bee stings, yellow jacket stings, brown recluse, black widow spider stings, and other spider bites, snake bites, fire ant bites, mosquito bites, chigger bites, and scorpion stings.

It is yet a further object of the present invention to provide a safe and inexpensive charcoal skin patch which is structured to deliver oxygen to the skin tissue for healing damaged skin tissue, such as in diabetic gangrene and burns.

It is still a further object of the present invention to provide a safe and inexpensive charcoal skin patch which is adapted to remove odor and adsorb infection from bedsores, diabetic ulcers, eczema, gum disease, teeth, kidney, liver, sinus, and around tubes for feeding or draining.

It is still a further object of the present invention to provide a safe and inexpensive charcoal skin patch which heals lesions on the skin by adsorbing bacteria, fungus, viruses, bacterial toxins, carcinogens, and products of allergies.

It is still a further object of the present invention to provide a safe and inexpensive charcoal skin patch which is adapted to reduce swelling of the skin by adsorbing excess tissue fluid and products of inflammation.

These and other objects and advantages of the invention are more readily apparent with reference to the detailed description and accompanying drawings.

SUMMARY OF THE INVENTION

The present invention is directed to a patch for topical application to the skin for the purpose of adsorbing toxins, bacteria, fungus, carcinogens, and other harmful pathogens in the treatment of bites, stings, injuries, disease and other disorders. The skin patch includes a charcoal based composition which is applied to an impervious backing sheet. In a preferred embodiment, the charcoal composition comprises activated charcoal combined with one or more host materials to produce a solid gel-like substance which can be sliced or otherwise formed as a layer of uniform thickness for application to the impervious backing sheet. In one embodiment, an enlarged surface of the charcoal composition is exposed, after removing a protective film, for direct application to the skin. In another embodiment, the layer of charcoal composition is covered by a permeable sheet such as paper (e.g. filter paper similar to that used in the manufacture of a tea bag). In yet another embodiment, the charcoal composition is contained within a porous container or envelope. The porous envelope may be made of paper, gauze, felt or other like materials.

In a preferred embodiment, the charcoal composition is comprised of activated charcoal combined with psyllium husk. Other suitable host materials are contemplated and are described hereinafter.

BRIEF DESCRIPTION OF THE DRAWINGS

For a fuller understanding of the nature of the present invention, reference should be made to the following detailed description taken in conjunction with the accompanying drawings in which.

Like reference numerals refer to like parts throughout the several views of the drawings.

DETAILED DESCRIPTION OF THE PREFERRED EMBODIMENTS

Figure 1:
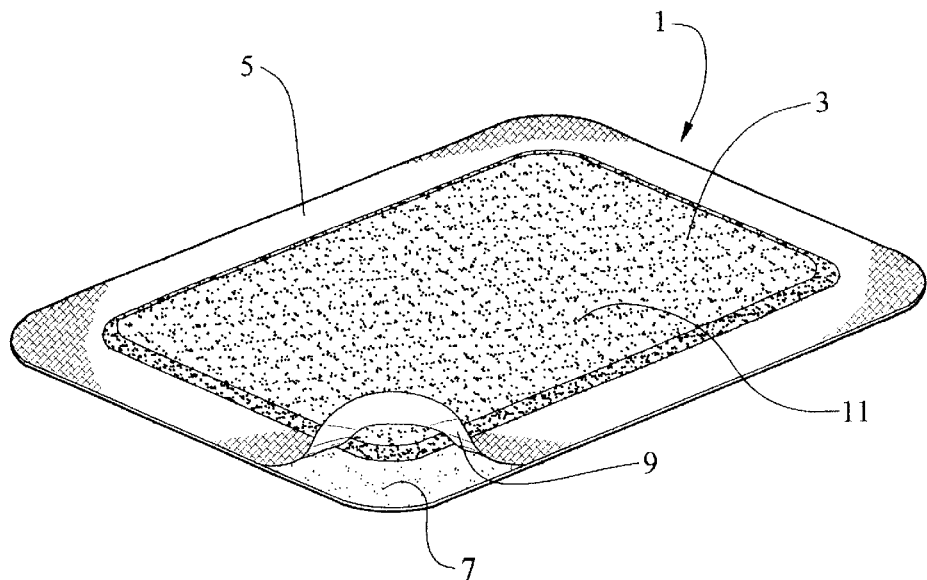
FIG. 1 is a top perspective view of one embodiment of the skin patch of the present invention.
Figure 2:
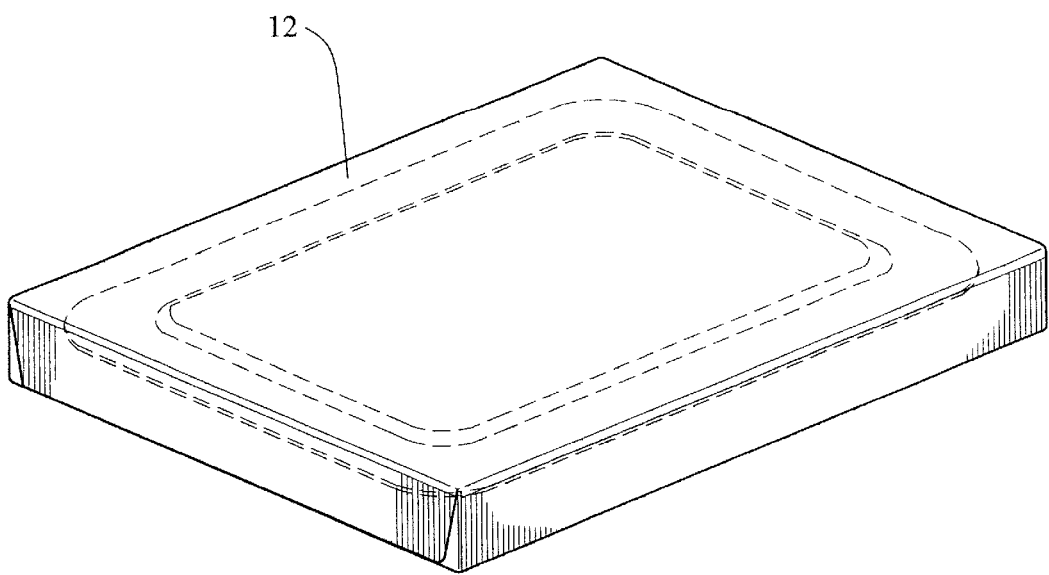
FIG. 2 is a top perspective view of a package for containing the skin patch of FIG. 1.

Referring initially to FIGS. 1 and 2, a first embodiment of the invention is shown. In FIG. 1, the skin patch, in accordance with one embodiment, is shown and is generally indicated as 1. The charcoal composition, comprising activated charcoal and a host material, is contained within a porous envelope 3, such as of paper, gauze or felt. The porous envelope 3 is applied to an impervious backing sheet 5 so that an outer adhesive surface 7 of the backing sheet surrounds the envelope 3. The outer adhesive 7 may either be pressure applicable to a skin surface, or can be moisture activated for the same purpose. If the adhesive is of a self-stick type, a peel-away protector strip 9 can be applied over the adhesive 7, and peeled away before the application of the patch to a body surface. When applied to the skin, the envelope 3 containing the charcoal composition of the present invention should cover the area being treated (e.g. bee sting, insect bite, poison ivy rash, open sore, etc.). It is important that the exposed surface 11 of the porous envelope 3 be structured and disposed to permit unobstructed transfer of toxins and other substances adsorbed by the charcoal composition. When applied to the skin, the impervious backing sheet faces away from the surface applied to the body, so that no moisture can escape from the envelope 3.

Suitably one or more skin patches of the type shown in FIG. 1 can be packaged in a water impermeable packaging 12 which may be structured for containing and maintaining the one or more skin patches in a wet or generally moist condition until the skin patch(s) is removed for use.

Figure 3:
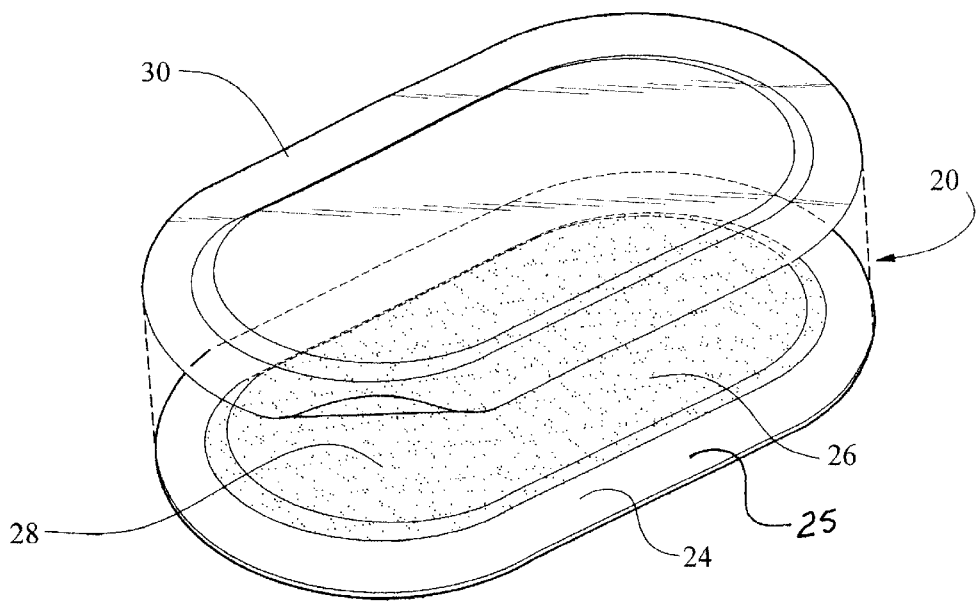
FIG. 3 is an exploded perspective view illustrating separation of a protective film from the skin patch in accordance with a preferred embodiment of the present invention.
Figure 5:
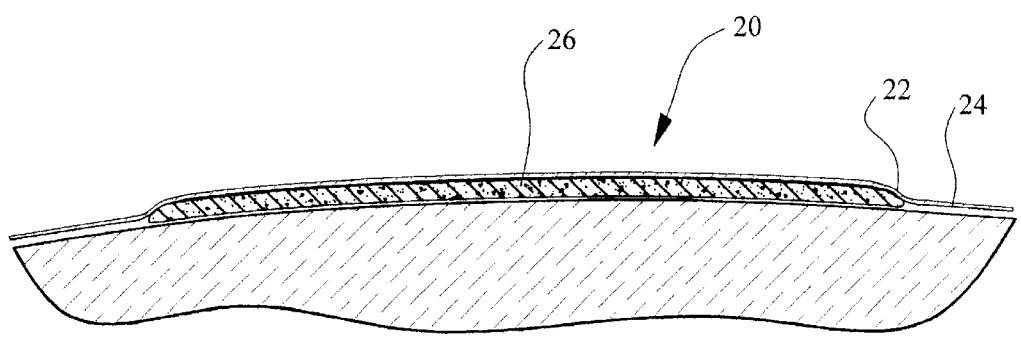
FIG. 5 is an isolated cross-sectional view showing the skin patch of FIG. 3 applied to the surface of the skin of a user in accordance with one embodiment thereof.

Referring to FIGS. 3 and 5, a preferred embodiment of the present invention is shown. Specifically, FIGS. 3 and 5 show the skin patch 20 to include an impervious backing sheet 24 with the activated charcoal composition 26 positioned thereon and surrounded by a peripheral zone 25 of the top side of the backing sheet. Preferably, the peripheral zone 25 includes an adhesive substance thereon similar to that described in connection with the embodiment of FIG. 1. A peel-away protective film 30 covers the peripheral zone 25 and the adhesive thereon, as well as the exposed surface 28 of the activated charcoal composition 26 in order to maintain moisture in the composition 26 and to protect the adhesive peripheral zone 25, particularly if the adhesive is of the self-stick type. Just prior to application of the skin patch 20 to the user's skin, the protective film 30 is removed to expose the adhesive on the peripheral zone 25 and the surface 28 of the activated charcoal composition. When applied to the skin, the exposed surface 28 of the charcoal composition 26 should cover the area being treated, in direct contact therewith. By applying slight pressure to the opposite side of the backing sheet 24, the adhesive on the outer peripheral zone 25 will removably adhere to the skin, thereby holding moisture between the backing sheet and the skin.

Figure 4:
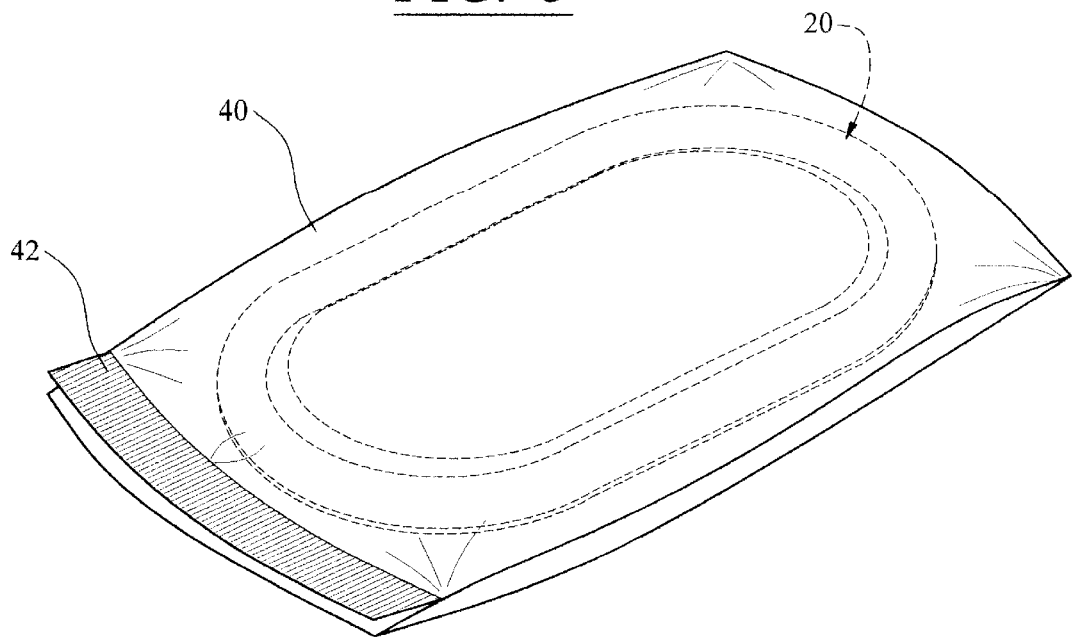
FIG. 4 is a perspective view illustrating a package for containing the skin patch of the embodiments shown in FIGS. 3 and 6.
Figure 6:
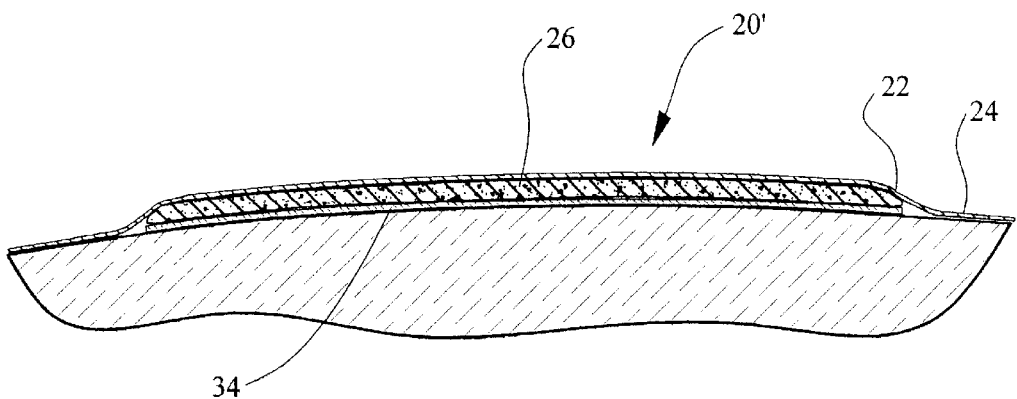
FIG. 6 is an isolated cross-sectional view showing an alternative embodiment of the skin patch applied to the skin surface of a user.

FIG. 4 illustrates a suitable package for containing the skin patch in FIGS. 3 and 5, as well as the embodiment shown in FIG. 6. Specifically, the package is in the form of an envelope 40 formed of an air and liquid impervious material such as a plastic composition, aluminum or Mylar. In the packaging process, the skin patch 20 is received within the envelope 40 and the envelope 40 interior is exhausted of all air to create a vacuum therein. A vacuum seal 42 is provided to maintain the envelope package 40 airtight to thereby preserve the activated charcoal composition. Both the skin patch 20 and package interior should be sterile at the time of packaging.

Referring to FIG. 6, an alternative embodiment of the skin patch is shown and is generally indicated as 20'. In this particular embodiment, the normally exposed surface of the charcoal composition 26 is covered by a porous sheet 34. When applied to the skin, as seen in FIG. 6, the porous sheet 34 is positioned between the skin surface and the charcoal composition 26. The porous sheet 34 may be formed of a paper material, similar to that used for tea bags or filter in automatic drip coffee machines.

In the preferred embodiment, the charcoal composition comprises a wood base activated charcoal combined with a suitable host material to produce a generally solid gel-like substance which can be formed in a mold. The molded form of the activated charcoal composition can then be sliced into layers of generally uniform thickness, in accordance with the profile seen in the embodiments of FIGS. 5 and 6. Alternatively, the activated charcoal composition can be molded in the layered form, without subsequent slicing.

In a preferred embodiment, a suitable host material is psyllium husk. Other suitable host materials include: titanium oxide; zinc oxide; zinc silicate; calcium hydroxide; calcium silicate; aluminum oxide; aluminum silicate; silica gel; magnesium oxide; and magnesium silicate. Fuller's earth, talcum powder, kaolin, desert clay, river clay and molecular sieves should work as suitable host materials if a high purity grade is used. Further suitable host materials include: starches (e.g. corn starch, potato starch, or tapioca, instant or regular); and gels (e.g. vegetable or animal gelatins such as Knox or Emes Kosher Gels).

There are some gums which may also be suitable as host materials including: methyl cellulose and related cellulose products; pectin; xanhan gum; gum tragacanth; gum Arabic; gum agar; guar gum; locust bean; karaya gum; acacia; gum ghatti; xanthan gum; carrageenans; alginates; agaroid; aragum; caragum; colloids; and freedom gum.

The charcoal skin patches of the embodiment shown throughout FIGS. 1 through 6 are intended for topical application to the skin for the treatment of numerous skin conditions and disorders including, but not limited to: athlete's foot; bedsores; bee stings; boils; brown recluse; spider bites; bruises; burns; chigger bites; cuts; diabetic ulcers; disinfection and deodorizing of wounds; earaches; fire ant bites; gangrene; gout; gum infections; infected wounds and sores; inflammation; kidney and liver infections; menstrual cramps; migrate headaches; mosquito bites; nail fungus; post surgical wounds; scorpion stings; shingles; sinus infections; snake bites; sore throats; sprains and injuries; tennis elbow; tight muscles; and toothaches.

A preferred embodiment of the charcoal composition and method of manufacture of the skin patch of the present invention is set forth in the following example:

EXAMPLE 1

| Ingredients | Amount |
|---|---|
| Activated charcoal | 1 cup |
| Whole psyllim husk | 1 cup |
| Distilled water | 2 cups |

METHOD OF MANUFACTURE

1. In a non-porous container add two (2) cups of distilled water.
2. Add one (1) cup activated charcoal powder.
3. Add one (1) cup whole psyllium husk.
4. Mix together until fully blended.
5. Pack into a container or mold of desired form or shape.
6. Refrigerate or freeze for several hours until mixture is firm.
7. Remove formed mixture from container.
8. Slice the formed mixture to produce slices having a generally uniform thickness of approximately $1/32$–$1/16$ of an inch.
9. Attach slices to impervious backing sheets with or without adhesive peel strip.
10. Insert backing sheet with attached slice into moisture barrier packaging.
11. Vacuum seal package.

While the instant invention has been shown and described in accordance with preferred and practical embodiments thereof, it is recognized that departures from the instant disclosure are contemplated within the spirit and scope of the present invention as set forth in the following claims and as interpreted under the doctrine of equivalents.

What is claimed is:

1. A composition for topical application to the skin comprising:

adsorbent means for adsorbing toxins, bacteria, fungus, carcinogens and other harmful pathogens residing on or below the skin surface, and said adsorbent means including activated, charcoal; and psyllium husk as a host material.

2. A patch for topical application to the skin comprising:
an impervious backing sheet;
a composition on one side of said backing sheet, said composition comprising:
adsorbent means for adsorbing toxins, bacteria, fungus, carcinogens, and other harmful pathogens residing on or below the skin surface, and said adsorbent means including activated charcoal; and
psyllium husk as a host material.

3. The patch as recited in claim 2 wherein said backing sheet comprises an adhesive substance on a periphery of said one side and surrounding said composition.

4. The patch as recited in claim 3 further comprising a peel-away protective film for covering said adhesive substance on said periphery.

5. The patch as recited in claim 3 further comprising a peel-away protective film for covering said composition and said adhesive substance.

6. The patch as recited in claim 2 wherein said host material further comprises a fibrous cotton.

7. A patch for topical application to the skin comprising:
an impervious backing sheet;
a composition on one side of said backing sheet, said composition comprising:
activated charcoal; and
psyllium husk as a host material.

\* \* \* \* \*